United States Patent [19]

Sinderby et al.

[11] Patent Number: 5,671,752
[45] Date of Patent: Sep. 30, 1997

[54] DIAPHRAGM ELECTROMYOGRAPHY ANALYSIS METHOD AND SYSTEM

[75] Inventors: Christer Sinderby, Montréal; Alejandro Grassino, Westmount, both of Canada; Sven Friberg; Lars Lindström, both of Möindal, Sweden

[73] Assignee: Université de Montréal/The Royal Insitution for the advancement of Learning (McGill University), Montréal, Canada

[21] Appl. No.: 414,494

[22] Filed: Mar. 31, 1995

[51] Int. Cl.$^6$ .................................................. A61B 5/04
[52] U.S. Cl. ........................................... 128/733; 128/777
[58] Field of Search ............................... 128/733, 777, 128/774, 780

[56] References Cited

U.S. PATENT DOCUMENTS

| | | | |
|---|---|---|---|
| 4,213,467 | 7/1980 | Stulen et al. | 128/733 |
| 5,212,476 | 5/1993 | Moloney | 128/733 |
| 5,349,963 | 9/1994 | Eskelinen | 128/733 |

OTHER PUBLICATIONS

"The Role of the Human Diaphragm Configuration on the EMG Centre Frequency" Ruiz–Neto, P.P. 1993 ALA/ATS International Conference.

"The Role of Diaphragmatic Recruitment in EMG Signal Analysis" Weinberg, J. 1993 ALA/ATS International Conference.

"Automatic EMG Selection for Muscle Fatigue Diagnosis" Sinderby, C. 1993 ALA/ATS International Conference.

"Effect of Esophageal Electrode Distance from the Diaphragm on EMG Center Frequency" Beck, J. 1993 ALA/ATS International Conference.

"The Influence of Innervation Zones of Esophageal Recordings of Diaphragmatic EMG" Beck, J. 1994 ALA/ATS International Conference.

"Effect of Chest Wall Configuration on Esophageal Recordings of Diaphragm EMG" Beck, J. 1994 ALA/ATS International Conference.

"Effects of Chest Wall Configuration and Electrode Positioning on Human Diaphragmatic EMG" Beck, J. 1994 A Thesis submitted to the Faculty of Graduate Studies and Research.

*Primary Examiner*—Sam Rimell
*Assistant Examiner*—Pamela L. Wingood

[57] ABSTRACT

In the method and system for electromyographic analysis of a striated muscle, electromyographic signals produced by the muscle are detected by means of an array of electrodes passing through the center of the muscle depolarizing region. Each electromyographic signal comprises an electromyographic component and a noise component. The position of the center of the muscle depolarizing region is then determined by detecting a reversal of polarity of the electromyographic components of the signals. Finally, two signals of opposite polarities amongst the electromyographic signals are subtracted. The subtraction subtracts the noise components of the two signals from each other but adds the electromyographic components of the two signals together to produce an electromyographic signal of improved signal-to-noise ratio. Advantageously, the array of electrodes is a linear array of successive electrodes, the center of the muscle depolarizing region is located between the electrodes of a given pair of successive electrodes, and the two signals of opposite polarities detected through the two pairs of successive electrodes adjacent to the given pair on opposite sides thereof are subtracted.

11 Claims, 7 Drawing Sheets

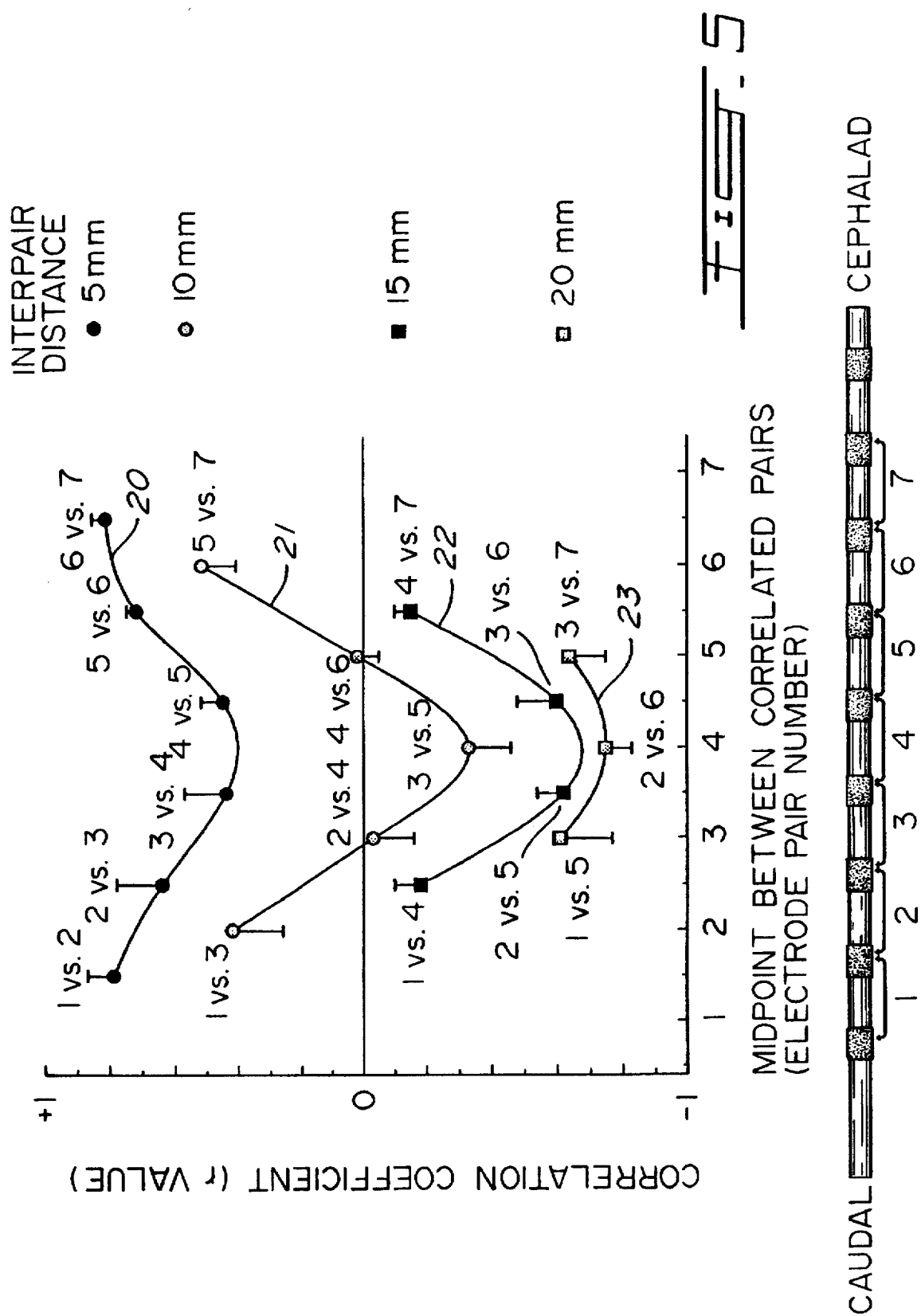

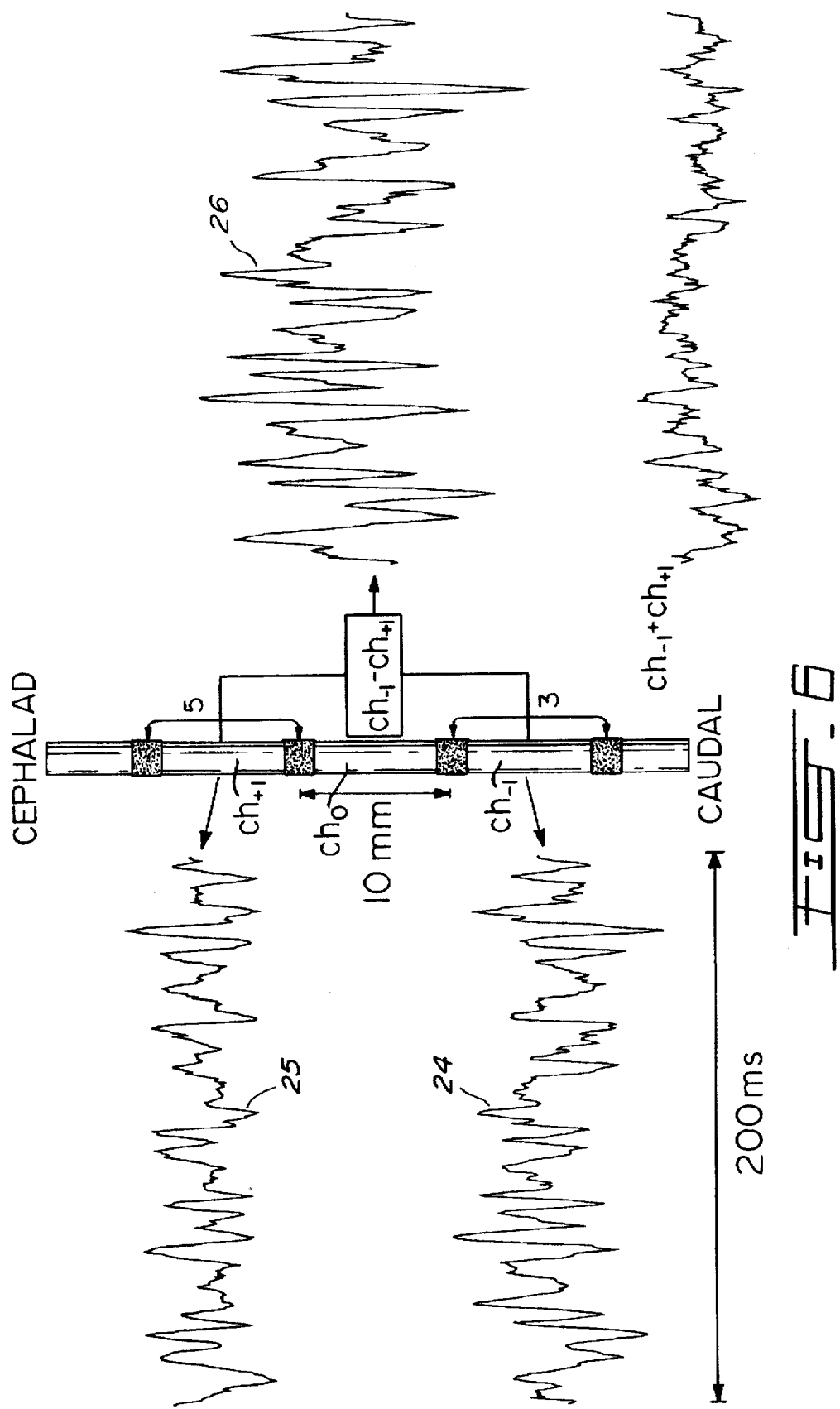

DIAPHRAGM ELECTROMYOGRAPHY ANALYSIS METHOD AND SYSTEM

BACKGROUND OF THE INVENTION

1. Field of the Invention

The present invention relates to an electromyography (EMG) analysis method and system in which EMG signals of reverse polarities obtained on opposite sides of the center of the striated muscle depolarizing region are subtracted to improve the signal-to-noise ratio.

2. Brief Description of the Prior Art

The physiological mechanisms which generate myoelectrical activity when a muscle contracts have been known and understood for a long time. In particular, how to record signals from the muscles is one of the most extensively, theoretically described topics in physiology. Although the theoretical understanding is impressive, the biophysiological application of these theories is, in practice, still deficient. As an example, no standardized analysis procedure has been developed for recording signals produced by activation of several, different motor units, the so called interference wave pattern. The interference wave pattern signal (electromyographic (EMG) signal) contains an immense quantity neuro-muscular function. However, as this EMG signal is amplified by a gain higher than 1000, it is affected by numerous artifacts. The influence of these artifacts varies in relation to the configuration of recording electrodes, the digitizing rate of the signal, and the type of recording technique.

Prior art analysis of interference wave pattern signals usually comprises a time consuming, tedious manual determination of the quality of the signal through visual inspection of this signal in the time domain. This determination is performed by a "subjective" investigator. Most of the prior art references describe how to calculate comparison estimates, but present very few comments on the signal quality. It is therefore not surprising to find that, in this technical field, independent studies evaluating the same questions have lead to different or even contradictory results.

OBJECTS OF THE INVENTION

An object of the present invention is therefore to overcome the above described drawbacks of the prior art.

SUMMARY OF THE INVENTION

More particularly, in accordance with the present invention, there is provided a method and system for producing an electromyographic signal having an improved signal-to-noise ratio and related to a striated muscle defining a muscle depolarizing region with a center. Electromyographic signals produced by the muscle are first detected by means of an array of electrodes passing through the center of the muscle depolarizing region. Each electrode-detected electromyographic signal comprises an electromyographic component and a noise component, and the position of the center of the muscle depolarizing region is detected through a reversal of polarity of the electromyographic component of the electrode-detected electromyographic signals. Finally, a first electromyographic signal detected by the electrodes of the array on a first side of the center of the muscle depolarization region is subtracted from a second electromyographic signal detected by the electrodes of the array on a second side, opposite to said first side, of the center of the muscle depolarization region. Since the first electromyographic signal has an electromyographic component of a first polarity, and since the second electromyographic signal has an electromyographic component of a second polarity opposite to the first polarity, the subtraction subtracts the noise components of the first and second electromyographic signals from each other but adds the respective electromyographic components of the first and second electromyographic signals together to produce the electromyographic signal of improved signal-to-noise ratio.

Advantageously, the position of the center of the muscle depolarizing region is detected by means of a cross-correlation on the electrode-detected electromyographic signals.

The subtraction may be made in the time domain or in the frequency domain. In the latter case, the first and second electromyographic signals are converted in the frequency domain before carrying out the subtraction.

The objects, advantages and other features of the present invention will become more apparent upon reading of the following non restrictive description of a preferred embodiment thereof, given by way of example only with reference to the accompanying drawings.

BRIEF DESCRIPTION OF THE DRAWINGS

In the appended drawings:

FIG. 5 is a graph showing the distribution of correlation coefficients calculated for determining the position of the center of the depolarizing region of the diaphragm along the array of electrodes of FIG. 2;

FIG. 6 is a schematic diagram illustrating in the time domain a double subtraction technique for improving the signal to noise ratio;

DETAILED DESCRIPTION OF THE PREFERRED EMBODIMENTS

Although the preferred embodiment of the present invention will be described hereinafter with relation to analysis of the EMG function of the diaphragm, it should be kept in mind that it can also be applied to other striated muscles.

Figure 1:
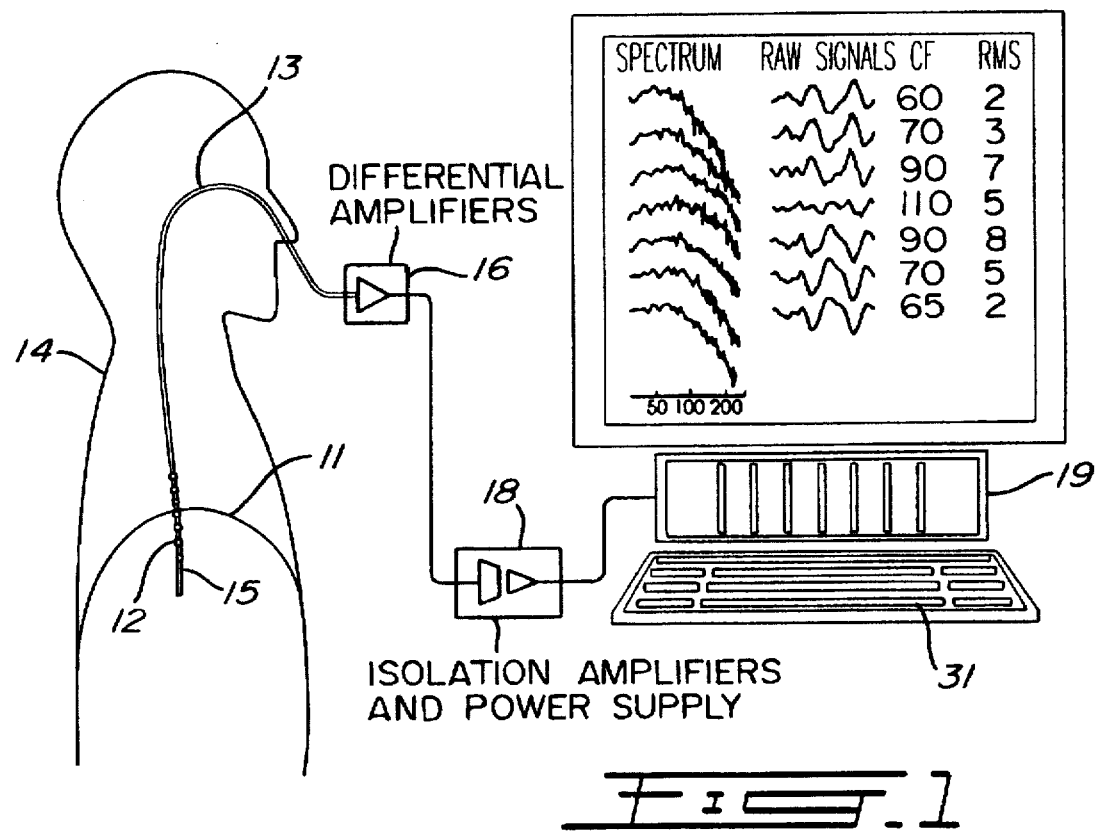
FIG. 1 is a schematic representation of a set-up of the EMG analysis system in accordance with the present invention.
Figure 2:
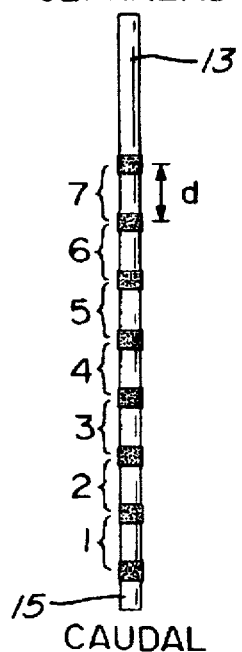
FIG. 2 is a section of oesophageal catheter on which an array of electrodes of the EMG analysis system of FIG. 1 is mounted.

To measure EMG activity of the diaphragm 11 (EMGdi) of a human patient 14, an array of electrodes such as 12 (FIGS. 1 and 2) are mounted on the free end section 15 of an oesophageal catheter 13, with a constant inter-electrode distance d (FIG. 2). As shown in FIG. 1, the catheter 13 is introduced into the patient's oesophagus through one nostril or the mouth until the array of electrodes 12 are situated at the level of the gastroesophageal junction. The diaphragm 11 and/or the oesophagus slightly move during breathing of the patient 14 whereby the array of electrodes 12 also slightly moves about the diaphragm 11. As will be explained in the following description, the method and system in accordance with the invention automatically compensate for this displacement.

To mount an electrode 12 on the free end section 15 of the catheter 13, stainless steel wire (not shown) may be wound around the catheter 13. The wound stainless steel wire presents a rough surface smoothed out by solder, which in turn is electroplated with nickel, copper and then gold or silver.

Electric wires (not shown) interconnect each pair of successive electrodes such as 1–7 (FIG. 2) with a respective one of a group of differential amplifiers 16. Obviously, these electric wires follow the catheter 13 from the respective electrodes 12 to the corresponding amplifiers 16, and are preferably integrated to the catheter 13. Preferably, the electric wires transmitting the EMGdi signals collected by the various pairs 1–7 of electrodes 12 are shielded to reduce the influence of external noise.

Figure 8:
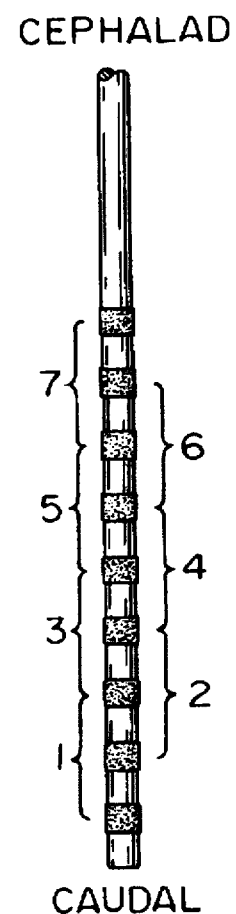
FIG. 8 illustrates a section of the oesophageal catheter of which a second embodiment of the array of electrodes is mounted.

In the illustrated example, the free end section 15 of the catheter 13 is provided with an array of eight electrodes 12 defining seven pairs 1, 2, 3, 4, 5, 6 and 7 of successive electrodes 12 respectively collecting seven different EMGdi signals. Although it has been found that EMG activity of the diaphragm (EMGdi) can be measured accurately with an oesophageal catheter 13 provided on the free end 12, it is within the scope of the present invention to use a different number of electrodes 12. Also, the pairs 1–7 do not need to be pairs of electrodes 1–7 as illustrated in FIG. 8; an array of nine electrodes is then required.

A major problem in recording EMGdi signals is to maintain the noise level as low and as constant as possible. Since the electric wires transmitting the EMGdo signals from the electrodes 12 to the differential amplifiers 16 act as an antenna, it is crucial, as indicated in the foregoing description, to shield these electric wires to thereby protect the EMGdi signals from additional artifactual noise. Also, the package enclosing the differential amplifiers 16 is made as small as possible and is positioned in close proximity to the patient's nose to decrease as much as possible the distance between the electrodes 12 and the amplifiers 16.

The amplified EMGdi signals are supplied to a computer 19 through respective isolation amplifiers of an amplifier and power supply unit 18. The unit 18 supplies electric power to the various electronic components of the differential and isolation amplifiers while ensuring adequate isolation of the patient's body from such power supply. The amplifier and power supply unit 18 also comprises low-pass filters included in the respective EMGdi signal channels to eliminate the effects of aliasing.

It is believed to be within the capacity of those of ordinary skill in the art to construct suitable differential amplifiers 16 and amplifier and power supply unit 18. Accordingly, the amplifiers 16 and the unit 18 will not be further described in the present specification.

Figure 3:
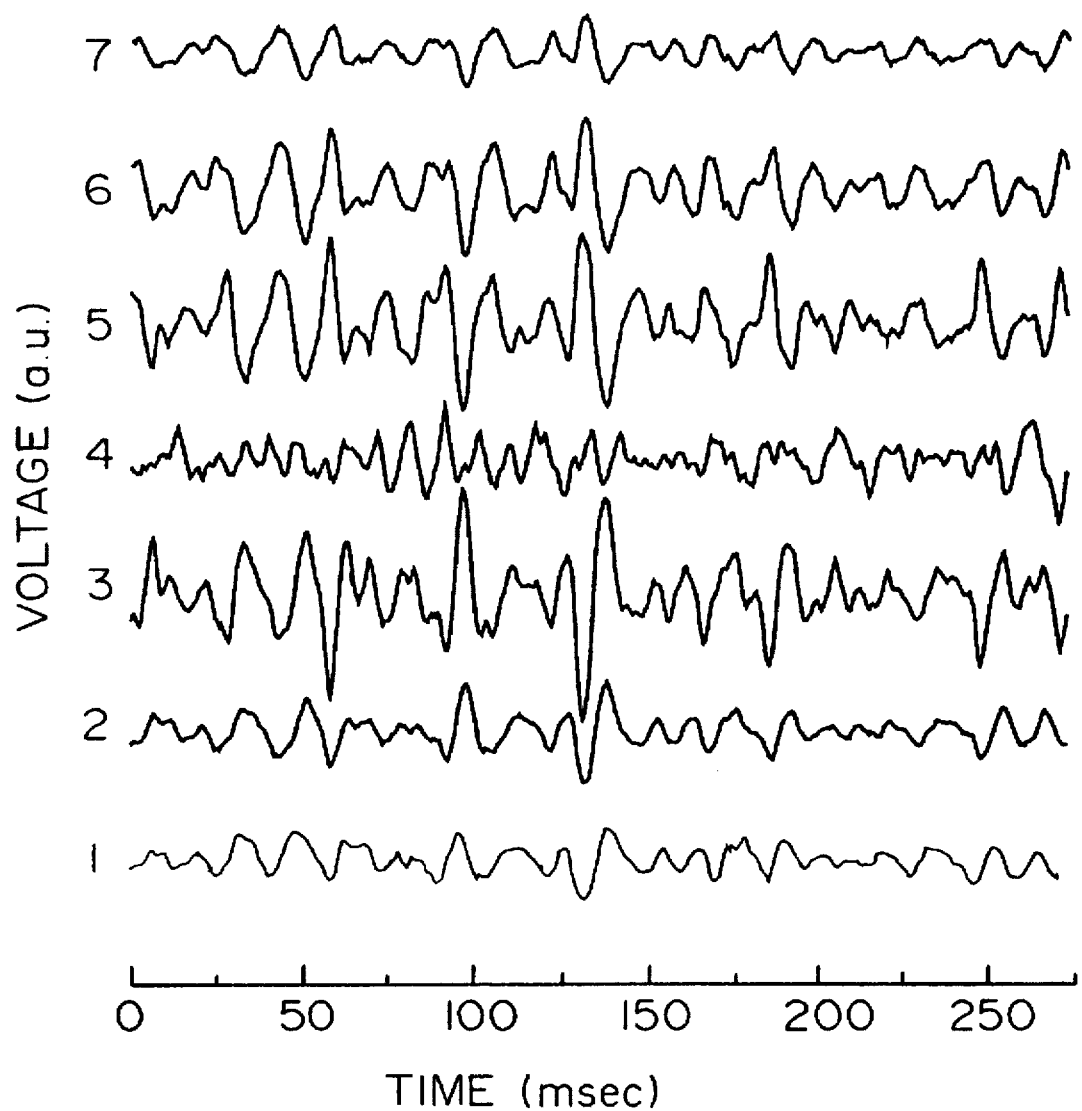
FIG. 3 is a graph showing a set of EMG signals of the diaphragm detected by pairs of successive electrodes of the array of FIG. 2.

An example of the seven EMGdi signals collected by the pairs 1–7 successive electrodes 12 and supplied to the computer 19 is illustrated in FIG. 3.

As the diaphragm is generally perpendicular to the longitudinal axis of the oesophageal catheter 13 equipped with an array of electrodes 12, only a portion of the electrodes 12 are situated in the vicinity of the diaphragm. It is therefore important to determine the position of the diaphragm with respect to the oesophageal electrode array.

The portion of the crural diaphragm 11 which forms the muscular tunnel through which the oesophageal catheter 13 is passed is referred to the "diaphragm depolarizing region" (DDR). The thickness of the DDR is 20–30 mm. It can be assumed that, within the DDR, the distribution of active muscle fibers has a center from which the majority of the EMGdi signals originate, i.e. the "diaphragm depolarizing region center" (DDR center). Therefore, EMGdi signals detected on opposite sides of the DDR center will be reversed in polarity with no phase shift; in other words, EMGdi signals obtained along the electrode array are reversing in polarity at the DDR center.

Moving centrally from the boundaries of the DDR, EMGdi power spectrums progressively attenuate and enhance in frequency. Reversal of signal polarity on either side of the electrode pair 4 with the most attenuated power spectrum confirms the position from which the EMGdi signals originate, the DDR center.

Figure 4:
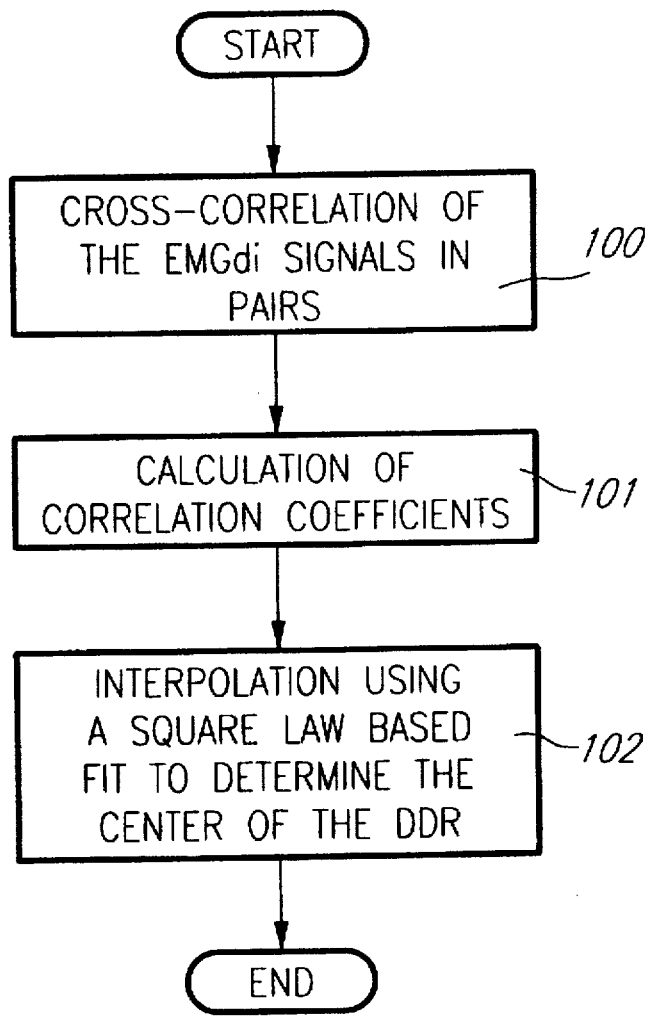
FIG. 4 is a flow chart showing a method for determining the position of the center of the depolarizing region of the diaphragm along the array of electrodes of FIG. 2.

The first task of the computer 19 is to determine the center of the DDR. For that purpose, a cross-correlation method is used (step 100 of FIG. 4). As well known to those of ordinary skill in the art, cross-correlation is a statistical determination of the phase relationship between two signals and essentially calculates the similarity between two signals in terms of a correlation coefficient r (step 101 of FIG. 4). A negative correlation coefficient r indicates that the cross-correlated signals are of opposite polarities.

FIG. 5 shows curves of the value of the correlation coefficient r versus the midpoint between the pairs of electrodes from which the correlated EMGdi signals originate. In this example, the inter-electrode distance is 10 mm. Curves are drawn for distances between the correlated pairs of electrodes 12 of 5 mm (curve 20), 10 mm (curve 21), 15 mm (curve 22) and 20 mm (curve 23). One can appreciate from FIG. 5 that negative correlation coefficient r are obtained when EMGdi signals from respective electrode pairs situated on opposite sides of the electrode pair 4 are cross-correlated. It therefore appears that the change in polarity occur in the region of electrode pair 4, which is confirmed by the curves of FIG. 3. Accordingly, it can be assumed that the center of the DDR is situated substantially midway between the electrodes 12 forming pair 4.

For example, the center of the DDR can be determined by interpolation (step 102 of FIG. 4) using a square law based fit of the three most negative correlation coefficients of curve 21 obtained by successive cross-correlation of the EMGdi signals from each electrode pair. Association of the center of the DDR to a pair of electrodes 12 provides a "reference position" from which to obtain EMGdi signals within the DDR. Such control is essential in overcomming the artifactual influence on the EMGdi power spectrum.

It has ben experimentally demonstrated that EMGdi signals recorded in the oesophagus are satisfactory as long as they are obtained from electrode pairs (with an inter-electrode distance situated between 5 and 20 mm) positioned at a distance situated between 5 and 30 mm on the opposite side of the DDR center (the inter-pair distance being therefore situated between 5 and 30 mm). Although EMGdi signals obtained from these positions offers a clear improvement in acceptance rate, the signal-to-noise ratio during quiet breathing still tends to remain unsatisfactorily low.

For example, in FIG. 3, the EMGdi signals originating from the electrode pairs 3 and 5 situated respectively 10 mm below and above the DDR are strongly inversely correlated at zero time delay. In contrast to the inversely correlated EMGdi signals, the noise components for electrode pairs 3 and 5 are likely to be positively correlated. Hence, as illustrated in FIG. 6, subtraction of the EMGdi signals 24 and 25 from electrode pairs 3 and 5 (step 200 of FIG. 8) will result into an addition of the corresponding EMGdi signals (signal 26) and into a subtraction, that is an elimination of the common noise components. This technique will be referred to as "the double subtraction technique".

Double subtraction technique can be carried out either in the time domain, or after conversion of signals 24 and 25 in the frequency domain. Double subtraction technique can be performed by subtracting other combinations of signals, for example by subtracting the EMGdi signal from electrode pair 2 from the EMGdi signal from electrode pair 5 (see FIG. 3), by subtracting signal from electrode pair 6 from the signal from electrode pair 3 and by adding these differences, etc. What is important is to subtract two signals of opposite polarities obtained in the vicinity of the muscle.

The increase in amplitude with double subtraction technique is associated with a twofold increase in RMS values. RMS values obtained by double subtraction technique are closely and linearly related to the original signals.

Figure 7:
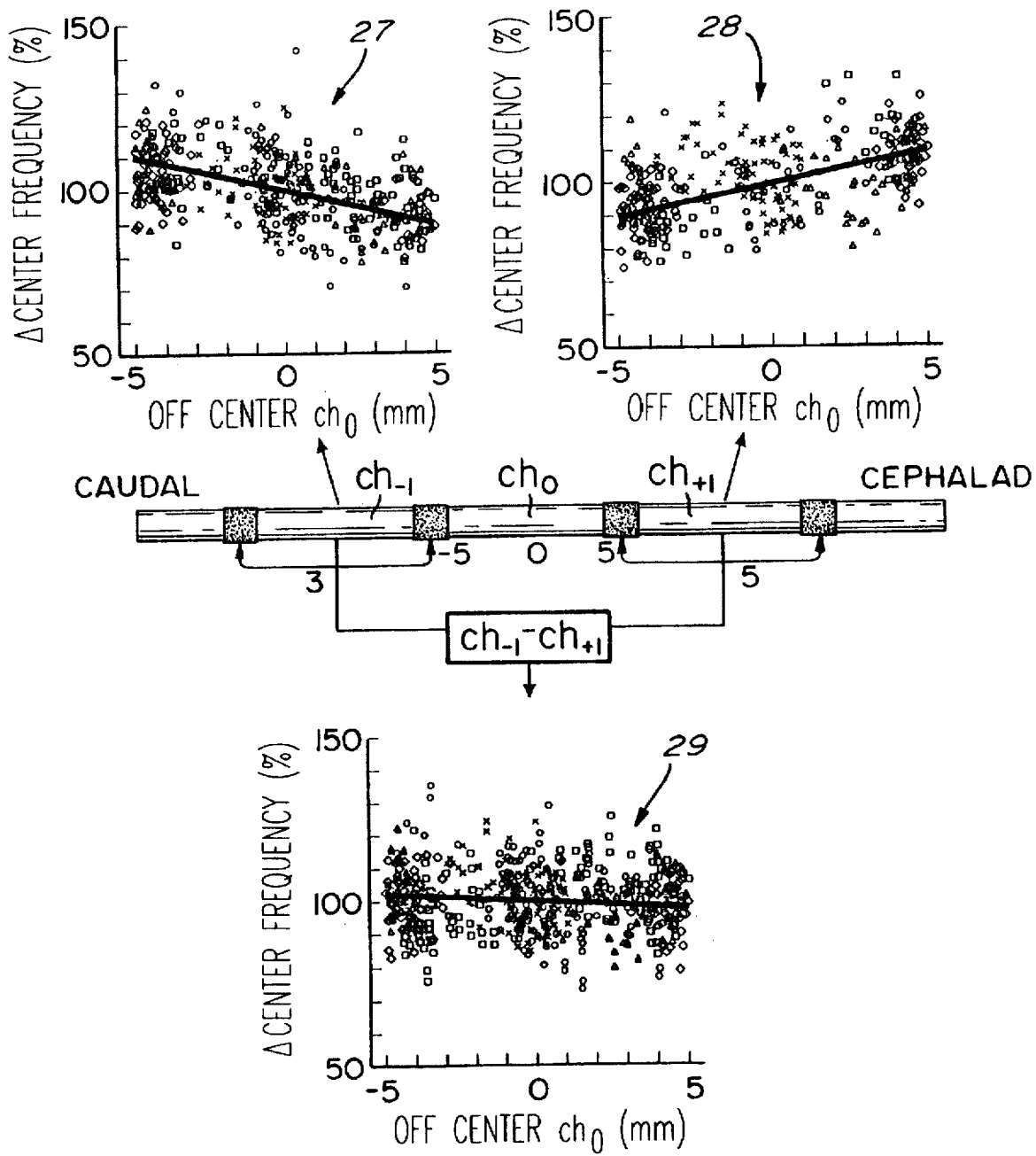
FIG. 7 is a schematic diagram illustrating in the frequency domain stabilization by the double subtraction technique of the center frequency upon displacement of the center of the depolarizing region of the diaphragm along the array of electrodes of FIG. 2.

In the frequency domain, means center frequency values for long time periods were not found to be significantly changed by the double subtraction technique. Moreover, the double subtraction technique compensates for the slight movement of the diaphragm 11 and/or the oesophagus during breathing of the patient 14 causing slight movement of the array of electrodes 12 about the diaphragm 11. Referring to FIG. 7, slight off center of the array of electrodes 12 causes a slight variation of mean center frequency values (see curves 27 and 28) for the EMGdi signals from the electrode pairs 3 and 5. The double subtraction technique eliminates such variation of mean center frequency values as indicated by curve 29. Therefore, the reciprocal influence of the position of the DDR center of the EMGdi signal frequency content is eliminated by the double subtraction technique.

It has been found that the double subtraction technique may improve the signal-to-noise ratio by more than 2 dB. Double subtraction technique is also responsible for a relative increase in acceptance rate by more than 30%.

Cross-talk signals from adjacent muscles are strongly correlated and equal in polarity. Hence, these cross-talk signals appear as a common mode signal for all electrode pairs and therefore, is eliminated by the double subtraction technique.

To eliminate the electrocardiogram (ECG) signal from EMGdi signal, the following automatic method of selecting EMGdi segments between ECGs is used.

Lung volume modify the shape and amplitude of the ECG for signals obtained with oesophageal electrodes. This is probably due to change in the electrode position and orientation with respect to the heart. Also, emotional and physical stress, and lung inflation may alter the heart rate. Cardiomyopathies can introduce other ECG abnormalities. In situation of loaded breathing, the EMGdi amplitude might exceed that of the ECG which makes it impossible to visually locate the QRS complexes in the EMGdi. Therefore, the inventors decided to use a separate recording of the ECG in order to be able to detect its presence. To avoid interference from the chest wall muscles, the ECG should preferably be recorded with electrodes placed 10 to 20 cm apart on the sternum in humans and by a catheter electrode placed in the jugular vein in animals. The ECG can also be obtained by adding all the EMGdi signals from the electrode array. This results in an approximately eight-fold increase of ECG amplitude and cancellation of the EMGdi signals.

In order to detect the R-wave of the QRS complex, the QRS wave was enhanced by applying a modified second order orthogonal Legnedre polynominal, which eliminates the DC level and low frequency slope of the ECG signal. Each modified R-wave was detected by an auto-adjusting function which triggers when the modified R-wave exceeds 75% of the weighted mean amplitude of the five previous modified R-waves. To maximize the size of the selected EMGdi sample under condition of varying heart rates, the ECG 38 and EMGdi 39 recordings were displayed on the computer monitor 40 with an R—R time interval normalized to 100%. By positioning two indicators on the computer screen, as indicated by the grey band 30 of FIG. 9, the size and location of the EMGdi sample, expressed as percentage of the R—R interval is manually selected and adjusted (step 301 of FIG. 9) by the investigator through the keyboard 31 (FIG. 1) of the computer 19.

Once the two indicators have been satisfactorily positioned, the analysis was executed and EMGdi samples throughout the entire recorded signal were selected within the percentage limits of the R—R interval. A raw signal 32 is thereby obtained (step 302 of FIG. 9). This approach allows for automatic EMGdi sample adjustment to be flexible with variation in the heart rate.

Figure 9:
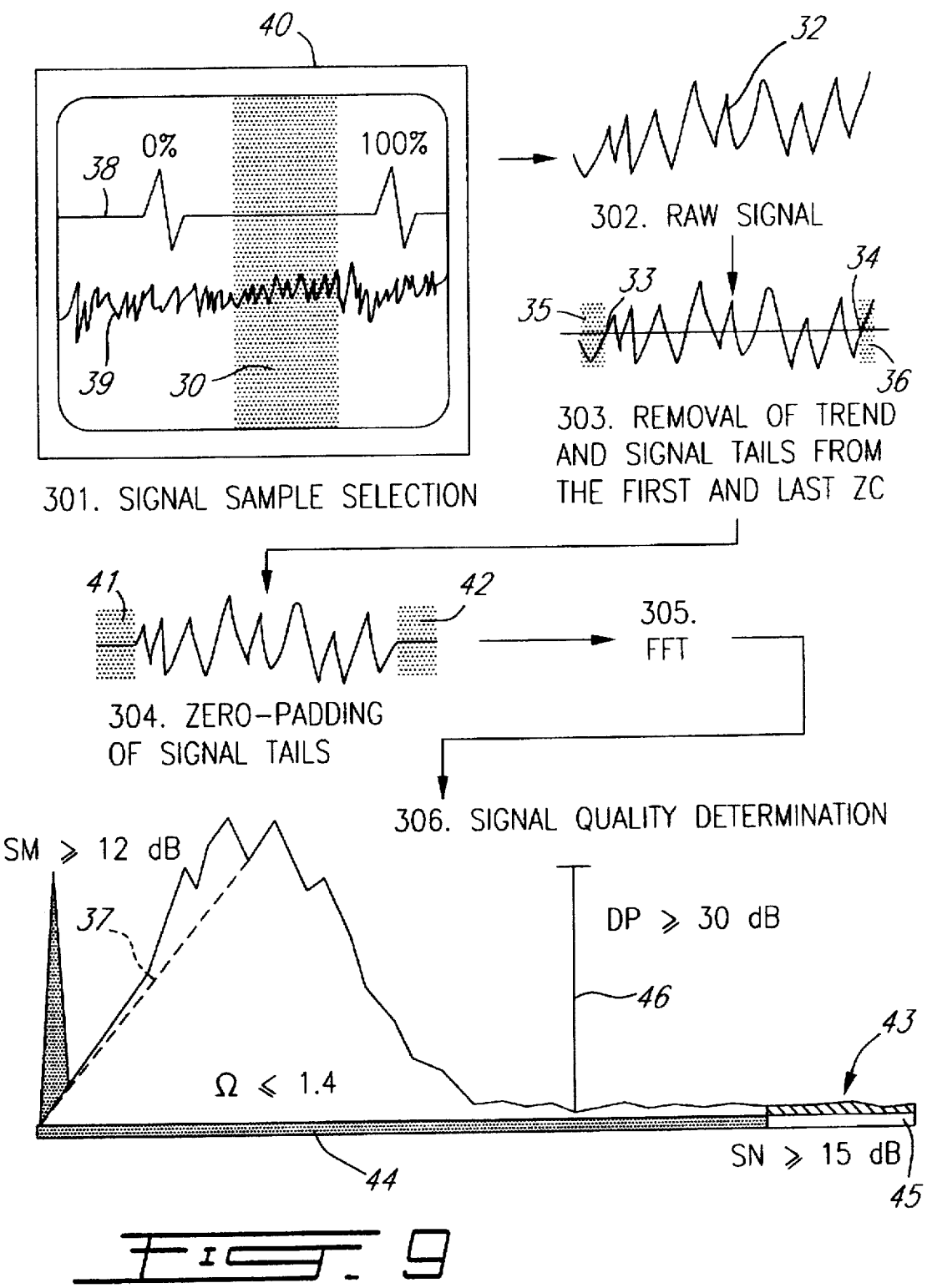
FIG. 9 is a flow chart showing treatment of the signal obtained by means of the above mentioned double subtraction technique.

In each selected EMGdi sample, the DC offset and the linear slope that is indictive of a motion artifact are removed by linear regression analysis (Step 303 of FIG. 9).

To fit the selected EMGdi samples of varying size into the array of a fixed size, used in the fast Fourier transform (FFT) carried out in step 305, the respective positions of the first 33 and last 34 zero-crossing are detected in the selected EMGdi sample. Then is carried out removal of the signal tails 35 and 36 from these first and last zero-crossing (step 303 of FIG. 9). From the position of the zero-crossings 33 and 34, the tails 35 and 36 of the selected EMG samples are then padded with the mean of the signal sample until the number of points required in the FFT array is reached (shaded areas 41 and 42 of step 304 of FIG. 9). Due to the previous removal of the DC level and the linear slope that is indicative of a motion artifact (step 303), mean values obtained were always equal to zero, and this technique will be referred to as zero-padding.

If the selected sample exceeds the size of the FFT array, which can occur when the heart rate is low, both tails of the EMGdi sample are symmetrically reduced to fit the array.

Determination of signal quality (step 306 of FIG. 9 is then carried out.

After removal of the ECG, EMGdi signals can still be contaminated by artifacts induced by motion of the electrodes (especially when positioned in the oesophagus), peristaltic contractions of the oesophagus, AC currents, and other noise. To automatically quantify the influence of these artifacts on the signal, four indices respectively describing the signal to motion artifact ratio, the signal to noise ratio, the spectrum maximum to minimum drop in power density ratio, and the power spectrum deformation were derived in the frequency domain to be used in step 306 of FIG. 9 to evaluate the quality, that is the degree of contamination of each selected EMGdi sample.

The Signal to Motion Artifact (SM) Ratio

Motion artifacts are defined as a low frequency fluctuation of the signal's DC level induced by mechanical alterations of the electrode metal to electrolyte interface i.e. changes in electrode contact area and/or changes in pressure that the tissue exerts on the electrode. The SM ratio is mainly based on two assumptions: (a) the frequency of the respiratory motion-induced DC fluctuations of the signal stay well below 20 Hz and (b) the shape of the non-contaminated EMGdi power spectrum is fairly linear between 0 and 20 Hz. According to these assumptions, the motion artifacts add power to the actual EMGdi power spectrum slope at frequencies below 20 Hz. To obtain the SM ratio, the sum of power densities for all frequencies was divided by the sum of power densities below 20 Hz that exceeded a straight line 37 (FIG. 9) between the zero frequency and the highest mean power density found. The highest mean power density represents the highest average power density of 13 consecutive points found when successively moving the average of 13 consecutive points from 35 to 600 Hz.

Tests on the SM ratio indicated that a lower level of 12 dB was appropriate to avoid underestimation of center frequency values by more than 5 Hz.

The Signal to Noise (SN) Ratio

The origin of noise is complex and is described to be caused by thermal effects, the quality of the amplifiers, and other external sources. Aliasing and leakage effects due to inappropriate high-pass filtering and digitizing rate will also add noise to the signal. Excluding aliasing and leakage, noise is defined as any signal of unidentifiable origin that can be detected in the high frequency range of the power spectrum. The assumptions used for the SN ratio are that noise has a constant power density over the frequency region of interest in the EMGdi recordings, and that no EMGdi activity related power is present in the in the upper 20% of the frequency range. Thus, the power for the upper 20% of the frequency range was first calculated. This is illustrated by the hatched area 43 in FIG. 9. The predicted total power of the noise is this power summed over the whole frequency range (dotted and non filled areas 44 and 45 below the power spectrum in FIG. 9. The SN ratio is then calculated as the ratio between the total EMGdi power and the total power of the noise. The SN ratio should be sensitive to all kinds of high frequency noise disturbances as well as to signals of low amplitude. However, it can produce falsely high values since it also includes the power in the low frequency region where motion artifacts and oesophageal peristalsis may produce significant power.

Tests indicate the SN ratio levels $\geq 15$ dB is sufficient to avoid an overestimation of center frequency values by more than 10 Hz, due to noise.

The Spectrum Maximum to Minimum Drop in Power Density (DP) Ratio

The DP ratio is obtained by dividing the highest mean power density of the spectrum by the power density represents the highest and lowest average power density of 13 consecutive points found when successively moving the average of 13 consecutive points from 35 to 600 Hz. The purpose of the DP ratio is to indicate whether the power spectrum is adequately peaked in the frequency range where the density is indicated by a vertical line 46 in FIG. 9). The DP ratio is thus sensitive to EMGdi amplitude and can detect the absence of EMGdi activity. In contrast to the SN ratio, the DP ratio is not sensitive to power below 35 Hz and therefore, will not reach falsely high values due to power induced by motion artifacts of EMGeso. Since the lowest mean power density is determined below 600 Hz, the application of the DP ratio also ensures that the EMGdi power density has dropped close to noise levels well before the upper frequency limit is reached. This is to avoid aliasing of the high frequency components due to under-sampling of the signal. Both the SM and DP ratios are dependent on correctly determining the highest mean power density and it is therefore crucial that low-pass filtering and shielding of the electrode wires prevent peaks in the power spectrum induced by disturbances from the mains or aliasing of signals containing high frequency disturbances.

Tests indicate that the DP ratio should be $\geq 30$ dB.

The Power Spectrum Deformation ($\Omega$) Ratio

Due to band-pass filtering, inter-electrode distance (in different recordings) and distance between muscle and electrode filtering effects, the EMGdi signal should normally describe a Gaussian distribution of power in the frequency range where the power of the actual diaphragm signal is distributed. At higher frequencies, the power levels should be very low. A ratio $\Omega$ to evaluate that the power spectrum actually corresponds to this distribution makes use of a power spectrum weighting functions calculated from the power spectral moments of order 0, 1 and 2 ($M_0$, $M_1$, $M_2$). Spectral moments are calculated by summation of the power density at each frequency multiplied by this frequency raised to a certain order. The ratio $\Omega$ is an index of spectral deformation, where $\Omega + (M_2/M_1)^{1/2}/(M_1/M_0)$. The ratio $\Omega$ is sensitive to changes in symmetry and peaking of the power spectrum and to additive disturbances in both the high and the low frequency region. This spectral deformation sensitive index is used to detect major disturbances of the spectrum, such as EMGeso or non-QRS complex related ECG activity in the signal. EMGeso or ECG activity produce significant power well above 20 Hz and are thus not necessarily detected by the SM ratio. A level of 1.3–1.4 appeared to be acceptable, and subsequent computer modelling and signal applications in the inventors' laboratory varified 1.4 as an appropriate upper level for this ratio. This ratio detected abnormal power spectrums induced by peristalsis of the oesophagus.

The sensitive numerical index to describe the power spectrum is the center frequency (CF). CF is obtained as the ratio between the power spectrum moment of order 1 and 0 ($M_1/M_0$). CF is thus strongly affected by both skewness of the power spectrum, as well as by low signal to noise ratios. To detect abnormal overestimations of CF, the ratio between CF and the median frequency (MF=the frequency at 50% $M_0$) indicated that if CF exceeds MF by more than 150%, the signals are unlikely to represent diaphragmatic activity.

AC current from surrounding power supplies adds power to the power spectrum at 50 or 60 Hz depending on the frequency used. This produces a very distinct peak in the power spectrum that can be quantified by taking the ratio between the mean value of the frequency used ±3 Hz and the predicted power at this frequency. The predicted power is obtained by calculating the slope between the AC current frequency −10 Hz to the AC current frequency +10 Hz excluding the 6 Hertz were the AC current is located. Selected EMGdi signal samples with unacceptable AC current levels can then either be excluded or the AC current can be replaced by predicted mean power at the original frequency and tis harmonics. From the inventors' experience, by using a shielded cable between the recording electrodes and the amplifiers 16 (FIG. 1), influence of the AC current from the network is if not completely eliminated, substantially reduced.

Determination of "Fatigue" Related Biological Phenomena

EMG power spectrum analysis has been for a long time used experimentally in the early detection of diaphragmatic fatigue. The trend seen during fatiguing contractions is a progressive shift towards lower frequencies of the power spectrum. The measurements used to describe this trend are the so called "high to low" frequency ratio, zero-crossing density, center-frequency, and median frequency. Regarding these measurements, a shift of the power spectrum towards lower frequencies will produce a decrease in the values obtained. The changes in these measurements seen with fatigue reflect to some extent the changes in the mean action potential conduction velocity. Thus, the most appropriate measure to describe changes seen during fatigue is the action potential velocity. Accurate determination of the mean action potential conduction velocity requires that the electrode array be oriented in the fiber direction and that no motor endplates are located under the array. It must also be stressed that cross-talk from adjacent muscles can affect conduction velocity measurements as well as the other frequency related measurements.

The mean action potential conduction velocity (CV) can be determined by two methods.

A first method is taking advantage of the bipolar electrode filtering function $\sin(\omega D/CV)=0$, for $\omega=n\pi CV/D$, where $n=0, 1, 2, \ldots$, $\omega$=angular frequency, D=half the inter-electrode distance. This function describes strong attenuation, "the first dip", at the frequency that corresponds to the mean action potential conduction velocity. Dips of higher order are also described at harmonics of the first dip. The location of the first dip is determined by the inter-electrode distance. The mean action potential conduction velocity can therefore be calculated as the product of the inter-electrode distance, and the frequency of the first dip in the power spectrum. The width of the dip will express the variance of the action potentials' mean conduction velocity. Since this method is very sensitive to electrode position, reorienting the electrode off the muscle fiber direction will result in the loss of conduction velocity related dips. Power spectrums obtained from half (D/2) and twice (2D) the inter-electrode distances of a reference inter-electrode distance (D) should theoretically place the first dip at twice (D/2) and half (2D) of the dip frequency obtained with the intermediate inter-electrode distance (D). For the different inter-electrode distances, the higher order dips in the spectrums should superimpose. From the multiple spectrums obtained, a model can be applied to determine both the location of the fist dips and their harmonics.

The second method to describe mean action potential conduction velocity is the cross-correlation technique. This technique is based on the time delay between signals from one electrode pair to the next, and again requires that the electrodes are oriented in the fiber direction. The time delay between the signals can then be determined either by cross-correlograms obtained from the time domain signals or by correlating different channels in the frequency domain.

When fiber direction is not known and innervation zones cannot be avoided, the methods for measurements of conduction velocity must be abandoned. Empirically, EMGdi power spectrum analysis still shows a shift towards lower frequencies during fatiguing contractions. However, to reduce the random variations of the spectrums obtained it is necessary to control as many variables as possible. With respect to measurements in the oesophagus it is possible to control distance between the muscle and the electrodes, position of the majority of motor end plates recruited, and influence of electrode motion artifacts and noise. There are also possibilities that cross-correlation and power spectrum dip techniques can give some information of changes in the fiber direction with respect to the electrodes. By implementing these algorithms, i.e. controlling the signal quality and the effects of filtering, the variation in the power spectrum can be drastically reduced. The use of linear regression analysis on the time function of center frequency does not demand more than some minutes of information for fatigue detection. These expectations have been met in controlled experiments using the signal quality indexes, and show encouraging results with respect to reproducibility and to reduction of stochastic variation in the signals and fatigue measurements.

Measuring diaphragm activity levels and fatigue, and bio-feedback, the system is ideal for use with ICU patients in order to optimize the ventilator support, and to diagnose diaphragm paralysis.

Although the present invention has been described hereinabove with reference to preferred embodiments thereof, these embodiments can be modified at will, within the scope of the appended claims, without departing from the spirit and nature of the subject invention.

What is claimed is:

1. A method for producing an electromyographic signal having an improved signal-to-noise ratio and related to a striated muscle defining a muscle depolarizing region with a center, comprising the steps of:

detecting electromyographic signals produced by the muscle by means of an array of electrodes passing through the center of the muscle depolarizing region, each electrode-detected electromyographic signal comprising an electromyographic component and a noise component;

detecting the position of the center of the muscle depolarizing region by detecting a reversal of polarity of the electromyograhic component of the electrode-detected electromyograhic signals; and subtracting a first electromyograhic signal detected by the electrodes of the array on a first side of the center of the muscle depolarization region, from a second electromyograhic signal detected by the electrodes of the array on a second side, opposite to said first side, of the center of the muscle depolarization region, wherein (a) the first electromyograhic signal has an electromyograhic component of a first polarity, (b) the second electromyograhic signal has an electromyograhic component of a second polarity opposite to said first polarity, (c) the subtraction subtracts the noise components of the first and second electromyograhic signals from each other but adds the respective electromyograhic components of said first and second electromyograhic signals together to produce said electromyograhic signal of improved signal-to-noise ratio.

2. A method for producing an electromyograhic signal having an improved signal-to-noise ratio as recited in claim 1, wherein said array of electrodes is a linear array of electrodes and defines a plurality of pairs of successive electrodes, wherein the center of the muscle depolarizing region is located between the electrodes of a given one of said pairs of successive electrodes, wherein said first electromyograhic signal is detected through the pair of successive electrodes adjacent to said given pair on one side of said given pair, and wherein said second electromyographic signal is detected through the pair of successive electrodes adjacent to said given pair on the other side of said given pair.

3. A system for producing an electromyographic signal having an improved signal-to-noise ratio and related to a striated muscle defining a muscle depolarizing region with a center, comprising:

an array of electrodes passing through the center of the muscle depolarizing region for detecting electromyographic signals produced by the muscle, each electrode-detected electromyographic signal comprising an electromyograhic component and a noise component;

means for detecting the position of the center of the muscle depolarizing region through a detection of a reversal of polarity of the electromyograhic component of said electrode-detected electromyograhic signals; and means for subtracting a first electromyograhic signal detected by the electrodes of the array on a first side of the center of the muscle depolarization region, from a second electromyograhic signal detected by the electrodes of the array on a second side, opposite to said first side, of the center of the muscle depolarization region, wherein (a) the first electromyograhic signal has an electromyograhic component of a first polarity, (b) the second electromyograhic signal has an electromyograhic component of a second polarity opposite to said first polarity, and (c) the subtraction subtracts the noise components of the first and second electromyograhic signals from each other but adds the respective electromyograhic components of said first and second electromyograhic signals together to produce said electromyograhic signal of improved signal-to-noise ratio.

4. A system for producing an electromyograhic signal having an improved signal-to-noise ratio as recited in claim 3, wherein said array of electrodes is a linear array of electrodes and defines a plurality of pairs of successive electrodes, wherein the center of the muscle depolarizing region is located between the electrodes of a given one of said pairs of successive electrodes, wherein said first electromyograhic signal is detected through the pair of successive electrodes adjacent to said given pair on one side of said given pair, and wherein said second electromyograhic signal is detected through the pair of successive electrodes adjacent to said given pair on the other side of said given pair.

5. A method for producing an electromyograhic signal having an improved signal-to-noise ratio as recited in claim 1, wherein said center position detecting step comprises conducting a cross-correlation on said electrode-detected electromyograhic signals.

6. A method for producing an electromyograhic signal having an improved signal-to-noise ratio as recited in claim 1, wherein said subtracting step is a time domain subtracting step.

7. A method for producing an electromyograhic signal having an improved signal-to-noise ratio as recited in claim 1, wherein said subtracting step comprises the step of converting said first and second electromyograhic signals in the frequency domain before carrying out the said substraction.

8. A system for producing an electromyograhic signal having an improved signal-to-noise ratio as recited in claim 3, wherein said center position detecting means comprises means for conducting a cross-correlation on said electrode-detected electromyographic signals.

9. A system for producing an electromyographic signal having an improved signal-to-noise ratio as recited in claim 3, wherein said subtracting means is a time domain subtracting means.

10. A system for producing an electromyographic signal having an improved signal-to-noise ratio as recited in claim 3, wherein said subtracting means comprises means for converting said first and second electromyographic signals in the frequency domain before carrying out the said substraction.

11. A system for producing an electromyographic signal having an improved signal-to-noise ratio as recited in claim 3, wherein said array of electrodes is mounted on a free end section of a catheter, and wherein each of said electrodes comprises a metallic wire wound around the catheter, said wound metallic wire presenting a rough surface first smoothed by solder, and then electroplated.

* * * * *